US011028237B2

(12) United States Patent
Kim et al.

(10) Patent No.: US 11,028,237 B2
(45) Date of Patent: Jun. 8, 2021

(54) METHOD FOR PREPARING SUPERABSORBENT POLYMER AND SUPERABSORBENT POLYMER PREPARED THEREBY

(71) Applicant: LG Chem, Ltd., Seoul (KR)

(72) Inventors: Taehee Kim, Daejeon (KR); Sewoo Yang, Daejeon (KR); Ji Young Hwang, Daejeon (KR); Gi Cheul Kim, Daejeon (KR)

(73) Assignee: LG Chem, Ltd.

( * ) Notice: Subject to any disclaimer, the term of this patent is extended or adjusted under 35 U.S.C. 154(b) by 143 days.

(21) Appl. No.: 16/341,804

(22) PCT Filed: Jun. 21, 2018

(86) PCT No.: PCT/KR2018/007028
§ 371 (c)(1),
(2) Date: Apr. 12, 2019

(87) PCT Pub. No.: WO2019/004653
PCT Pub. Date: Jan. 3, 2019

(65) Prior Publication Data
US 2019/0315930 A1    Oct. 17, 2019

(30) Foreign Application Priority Data

Jun. 30, 2017 (KR) .................. 10-2017-0083849
Jun. 20, 2018 (KR) .................. 10-2018-0071073

(51) Int. Cl.
*C08J 3/075* (2006.01)
*B01J 20/26* (2006.01)
(Continued)

(52) U.S. Cl.
CPC ............. *C08J 3/075* (2013.01); *B01J 20/267* (2013.01); *B01J 20/28047* (2013.01);
(Continued)

(58) Field of Classification Search
CPC ..... C08J 3/075; C08J 3/12; C08J 3/245; C08J 2333/14; C08J 2471/02; C08J 3/24;
(Continued)

(56) References Cited

U.S. PATENT DOCUMENTS 5,064,582 A    11/1991   Sutton et al.
5,112,902 A    5/1992    Moriya et al.
(Continued)

FOREIGN PATENT DOCUMENTS

EP    0885917 A2    12/1998
EP    1690887 A1    8/2006
(Continued)

OTHER PUBLICATIONS

International Search Report for PCT/KR2018/007028, dated Oct. 17, 2018.
(Continued)

*Primary Examiner* — Robert C Boyle
(74) *Attorney, Agent, or Firm* — Lerner, David, Littenberg, Krumholz & Mentlik, LLP

(57) ABSTRACT

The present invention relates to a method for preparing a superabsorbent polymer that progresses dry mixing of fine powders and a specific powder type of polymer binder when reassembling fine powders generated during the preparation process of a superabsorbent polymer, and thus obviates the necessity for a moisture drying process after reassembling fine powders, thereby reducing thermal losses, improving productivity, and obtaining a superabsorbent polymer having excellent basic absorption properties, and a superabsorbent polymer prepared by the method.

13 Claims, 1 Drawing Sheet

(51) Int. Cl.
    *B01J 20/28* (2006.01)
    *B01J 20/30* (2006.01)
    *C08J 3/12* (2006.01)
    *C08J 3/24* (2006.01)

(52) U.S. Cl.
    CPC ....... *B01J 20/3028* (2013.01); *B01J 20/3042* (2013.01); *B01J 20/3085* (2013.01); *C08J 3/12* (2013.01); *C08J 3/245* (2013.01); *B01J 2220/68* (2013.01); *C08J 2333/14* (2013.01); *C08J 2471/02* (2013.01)

(58) Field of Classification Search
    CPC ................ B01J 20/267; B01J 20/28047; B01J 20/3028; B01J 20/3042; B01J 20/3085; B01J 2220/68; A61L 15/60; C08F 220/06; C08L 71/02
    See application file for complete search history.

(56) References Cited

U.S. PATENT DOCUMENTS

| | | | |
|---|---|---|---|
| 5,248,709 A * | 9/1993 | Brehm | A61L 15/60 427/180 |
| 5,373,054 A | 12/1994 | Sanuki et al. | |
| 6,133,193 A | 10/2000 | Kajikawa et al. | |
| 6,143,821 A * | 11/2000 | Houben | A61L 15/60 524/557 |
| 2006/0183828 A1* | 8/2006 | Dairoku | B01J 20/30 524/155 |
| 2007/0015860 A1 | 1/2007 | Frank | |
| 2007/0066754 A1 | 3/2007 | Loeker et al. | |
| 2008/0075937 A1 | 3/2008 | Wada et al. | |
| 2012/0267570 A1 | 10/2012 | Shi et al. | |
| 2013/0102750 A1 | 4/2013 | Watanabe et al. | |
| 2014/0306156 A1 | 10/2014 | Tian et al. | |
| 2015/0259522 A1 | 7/2015 | Lee et al. | |
| 2015/0229522 A1 | 8/2015 | Poutievski et al. | |
| 2016/0311985 A1 | 10/2016 | Jung et al. | |
| 2017/0166707 A1 | 6/2017 | Jang et al. | |
| 2017/0216815 A1 | 8/2017 | Jang et al. | |
| 2017/0226248 A1 | 8/2017 | Kim et al. | |
| 2017/0226295 A1 | 8/2017 | Kim et al. | |

FOREIGN PATENT DOCUMENTS

| | | |
|---|---|---|
| EP | 3225649 A1 | 10/2017 |
| EP | 3333198 A1 | 6/2018 |
| JP | H05507511 A | 10/1993 |
| JP | H08113653 A | 5/1996 |
| JP | 2006116535 A | 5/2006 |
| JP | 2008018328 A | 1/2008 |
| JP | 2008526502 A | 7/2008 |
| JP | 2016514761 A | 5/2016 |
| KR | 100269980 B1 | 10/2000 |
| KR | 20140026511 A | 3/2014 |
| KR | 20140063457 A | 5/2014 |
| KR | 20160041826 A | 4/2016 |
| KR | 20160144902 A | 12/2016 |
| KR | 101700907 B1 | 1/2017 |
| KR | 20170009546 A | 1/2017 |
| WO | 9118042 A1 | 11/1991 |
| WO | 2006078046 A2 | 7/2006 |
| WO | 2006101271 A1 | 9/2006 |
| WO | 2011136301 A1 | 11/2011 |
| WO | 2016056866 A1 | 4/2016 |
| WO | 2016056867 A1 | 4/2016 |
| WO | 2017078369 A1 | 5/2017 |

OTHER PUBLICATIONS

Odian, George, "Principles of Polymerization", Second Edition, John Wiley & Sons, 1981, 3 pages.
Schwalm, Reinhold, "UV Coatings: Basics, Recent Developments and New Applications", Elsevier, Dec. 2006, 3 pages.
Japanese Search Report for Application No. 2019506089 dated Feb. 19, 2020, 9 pages.
Buchholz, et al., Modern Superabsorbent Polymer Technology, 1998, pp. 1-44.
Extended European Search Report including Written Opinion for Application No. EP18822675.7 dated Sep. 9, 2019, pp. 1-10.
Third Party Observation for PCT/KR2018/007028 submitted Sep. 19, 2019.

\* cited by examiner

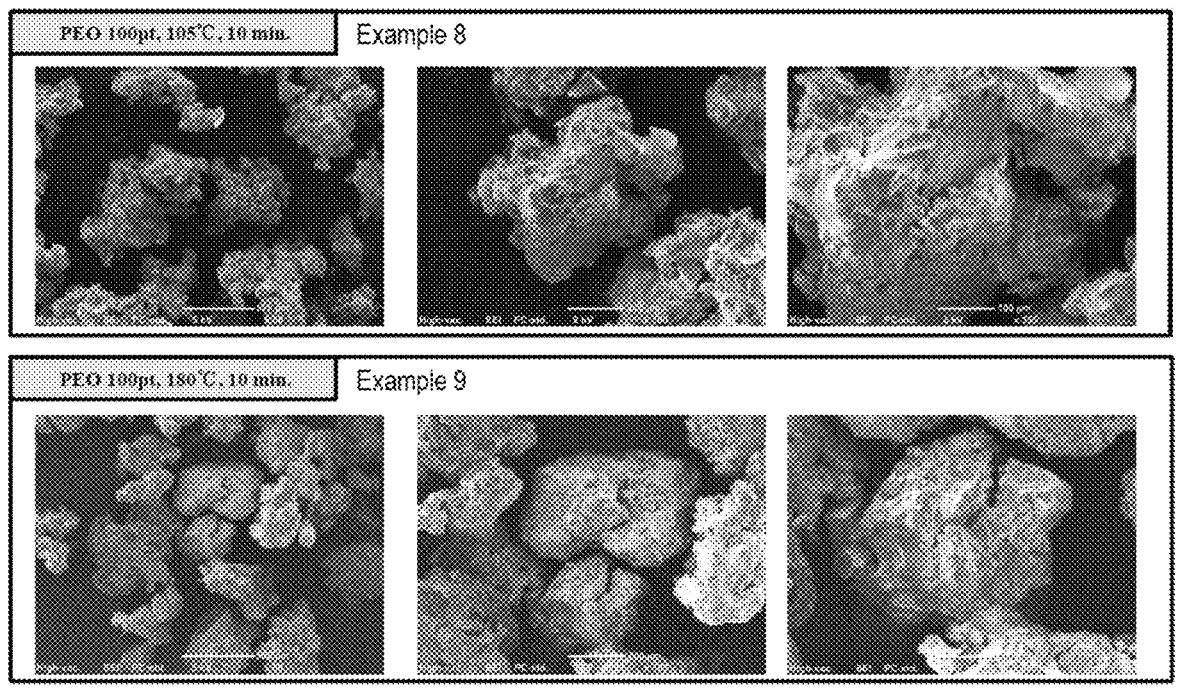

METHOD FOR PREPARING SUPERABSORBENT POLYMER AND SUPERABSORBENT POLYMER PREPARED THEREBY

CROSS-REFERENCE TO RELATED APPLICATION(S)

This application is a national phase entry under 35 U.S.C. § 371 of International Application No. PCT/KR2018/007028, filed Jun. 21, 2018, which claims priority to Korean Patent Application No. 10-2017-0083849 filed Jun. 30, 2017 and Korean Patent Application No. 10-2018-0071073 filed Jun. 20, 2018, the disclosures of which are herein incorporated by reference in their entirety.

TECHNICAL FIELD

The present invention relates to a method for preparing a superabsorbent polymer that can prepare superabsorbent polymer having excellent basic absorption performance, reduce thermal losses during the process of reassembling fine powders, and improve the productivity, and a superabsorbent polymer prepared thereby.

BACKGROUND OF ART

A superabsorbent polymer (SAP) is a synthetic polymer material that can absorb moisture of 500 to 1000 times its own weight, and is also called a superabsorbent material (SAM), an absorbent gel material (AGM), etc. according to developing companies. The superabsorbent polymer began to be commercialized for sanitary items, and currently, it is being widely used for hygienic goods such as disposable diapers and so on, water-holding materials for soil, water stop materials for civil engineering and architecture, sheets for raising seedlings, freshness preservatives in the field of food circulation, fomentation materials, etc.

Such superabsorbent polymer may be generally prepared in the form of powders by preparing a hydrogel polymer through the polymerization process of monomers, grinding, drying, and sieving it to prepare base polymer powders, and then progressing surface crosslinking. Here, the grinding of the hydrogel polymer is required to prepare a superabsorbent polymer in the form of powders or particles, but during the process, fine powders having a size of less than a standard size are generated.

The size of normal superabsorbent polymer particles may become about 150 μm to 850 μm or about 300 μm to 500 μm in the production process, and polyacrylic acid (PAA) particles having a size of less than a standard size, generated during the production process of the superabsorbent polymer, are referred to as "powders". Since such fine powders of the superabsorbent polymer are generated at a rate of about 10 to 15% of the total polymer product, there is a need to reassemble them for improvement in productivity.

However, the fine powders act as one of factors decreasing the productivity, and particularly, thermal losses are generated during reassembling the fine powders of the superabsorbent polymer.

In the previous method, in order to reassemble fine powders of the superabsorbent polymer, water with a moisture content of about 55% or more is required, and enormous thermal losses are generated to dry it.

Therefore, it is important to reduce the thermal losses generated during the reassembly of fine powders to improve the productivity of the production facilities of the superabsorbent polymer.

However, up to now, the development of a method that can improve the productivity in the process of reassembling fine powders, and effectively reduce thermal losses, has been unsatisfactory.

DETAILED DESCRIPTION OF THE INVENTION

Technical Problem

It is on object of the present invention to provide a method for preparing a superabsorbent polymer that can reduce thermal losses generated when reassembling fine powders during an existing preparation process of a superabsorbent polymer, and efficiently recycling fine powders to improve the productivity of a superabsorbent polymer having excellent properties, and a superabsorbent polymer prepared thereby.

Technical Solution

The present invention provides a method for preparing superabsorbent polymer, including steps of:
conducting crosslinking polymerization of water soluble ethylenically unsaturated monomers having acid groups of which at least a part are neutralized, in the presence of an internal crosslinking agent, to form hydrogel polymer including a first crosslinked polymer;
gel grinding the hydrogel polymer;
drying the gel ground hydrogel polymer, and grinding and sieving the dried product of the hydrogel polymer to form base polymer powders; and
heat treating the base polymer powders to progress surface crosslinking, in the presence of a surface crosslinking agent,
wherein the method further includes steps of:
recovering fine powders, after sieving the dried product of the hydrogel polymer;
reassembling the fine powders in the presence of a powder type of polymer binder to provide reassembled fine powders; and
mixing the reassembled fine powders with the hydrogel polymer before drying.

The present invention also provides a superabsorbent polymer including: base polymer powders including a first crosslinked polymer of water soluble ethylenically unsaturated monomers having acid groups of which at least a part are neutralized; and
a surface crosslink layer formed on the base polymer powders, and including second crosslinked polymer in which the first crosslinked polymer is additionally crosslinked by a surface crosslinking agent,
wherein a centrifuge retention capacity (CRC) for a saline solution (0.9 wt % sodium chloride aqueous solution) for 30 minutes is 30 g/g to 45 g/g.

Hereinafter, a method for preparing a superabsorbent polymer and a superabsorbent polymer prepared thereby according to specific embodiments of the present invention will be explained in detail. However, these are presented only as illustrations of the present invention, the scope of the right of the invention is not limited thereby, and it is obvious to one of ordinary skill in the art that various modifications can be made to the embodiments within the scope of the right of the invention.

Throughout the specification, unless specifically mentioned, the term "comprising" or "containing" means to include any construction element (or constructional components) without specific limitations, and it cannot be interpreted as excluding the addition of other construction elements (or constructional components).

Throughout the specification, a weight average molecular weight means a weight average molecular weight (unit: g/mol) in terms of polystyrene, measured by the CPG method. During the process of measuring a weight average molecular weight in terms of polystyrene, measured by the GPC method, detectors and analysis columns such as commonly known analyzers and refractive index detectors, etc. may be used, and commonly used temperature conditions, solvents, and flow rates may be applied. Specific examples of the measurement conditions may include a temperature of 35° C., THF (tetrahydrofuran), and a flow rate of 1 mL/min.

According to one embodiment of the invention, a method for preparing a superabsorbent polymer is provided, which includes steps of: conducting crosslinking polymerization of water soluble ethylenically unsaturated monomers having acid groups of which at least a part are neutralized, in the presence of an internal crosslinking agent, to form a hydrogel polymer including a first crosslinked polymer; gel grinding the hydrogel polymer; drying the gel ground hydrogel polymer, and grinding and sieving the dried product of the hydrogel polymer to form base polymer powders; and heat treating the base polymer powders to progress surface crosslinking, in the presence of a surface crosslinking agent, wherein the method further includes steps of: recovering fine powders, after sieving the dried product of the hydrogel polymer; reassembling the fine powders in the presence of a powder type of polymer binder to provide reassembled fine powders; and mixing the reassembled fine powders with the hydrogel polymer before drying.

Previously, since water was used when reassembling SAP fine powders, a process of moisture drying was required in the subsequent process. However, in the present invention, water is not used when reassembling fine powders of the superabsorbent polymer, and a specific powder type of polymer binder is used under a solvent-free condition. Thus, in the present invention, since a moisture drying process which had to be used when reassembling fine powders is not necessary, thermal losses can be reduced and productivity and workability can be largely improved. That is, since the polymer binder is dry-mixed in the state of powders when mixed with fine powders of the superabsorbent polymer, there is no need to use separate water.

That is, in the previous fine powder reassembly process, even if a binder is used, an aqueous solution of a binder is prepared, and then fine powders and the aqueous solution of a binder are mixed, and a fine powder reassembly process is conducted, and then a moisture drying process of reassembled fine powders is conducted. However, since such a method requires a separate drying process, a drier should be involved, and thermal losses may be generated.

However, in the present invention, after progressing dry mixing of fine powders and a powder type of polymer binder, even if heat treatment is progressed for a short time, reassembled fine powders can be formed. Thus, the present invention can improve both workability and productivity compared to the existing method.

Further, polyethylene oxide is used as the specific polymer binder, which has an excellent effect of reassembling fine powders compared to the previously known compounds such as polypropylene glycol, polyethylene glycol, etc.

Hereinafter, a method for preparing a superabsorbent polymer including a fine powder reassembly process according to one embodiment of the present invention will be explained in detail.

The method for preparing a superabsorbent polymer of the present invention includes steps of: conducting crosslinking polymerization of water soluble ethylenically unsaturated monomers having acid groups of which at least a part are neutralized, in the presence of an internal crosslinking agent, to form a hydrogel polymer including first crosslinked polymer; gel grinding the hydrogel polymer; drying the gel ground hydrogel polymer, and grinding and sieving the dried product of the hydrogel polymer to form base polymer powders; and heat treating the base polymer powders to progress surface crosslinking, in the presence of a surface crosslinking agent.

In the present invention, after the gel grinding step of the hydrogel polymer, drying, grinding, and sieving processes are undertaken, and then fine powders are recovered, and the recovered fine powders are passed through a reassembly process and are re-introduced into a process of the gel ground hydrogel polymer, and thus, can be used for preparing base polymer powders through the subsequent processes.

The 'first crosslinked polymer' means a polymer formed by the crosslinking polymerization of the above-explained water soluble ethylenically unsaturated monomers in the presence of an internal crosslinking agent, and the 'base polymer powders' mean materials including such first crosslinked polymer. Further, the 'second crosslinked polymer' means a material in which the first crosslinked polymer is additionally crosslinked by a surface crosslinking agent, and thus, it is formed on the base polymer powders. The surface crosslinking agent will be explained below.

As used herein, the fine powders of the superabsorbent polymer may include fine powders having an average particle diameter of less than 150 μm, obtained in the step of forming base polymer powders having an average particle diameter of 150 μm to 850 μm or about 300 μm to 500 μm, during the processes of drying, grinding, and sieving the hydrogel polymer.

The 'superabsorbent polymer' means base polymer powders including a first crosslinked polymer of water soluble ethylenically unsaturated monomers having acid groups of which at least a part are neutralized, and a surface crosslink layer formed on the base polymer powders, and including a second crosslinked polymer in which the first crosslinked polymer is additionally crosslinked by a surface crosslinking agent.

Thus, in the present invention, the fine powders are recovered and reused in the preparation process of the superabsorbent polymer.

Hereinafter, the preparation process will be explained in more detail according to each step.

First, the step of forming the hydrogel polymer, the step of forming the base polymer powders, and the step of treating the surface of the base polymer powders may be progressed according to the methods described below, and the process of reassembling fine powders will be explained first.

As described below, the hydrogel polymer is obtained according to the preparation process of the superabsorbent polymer, and then it is gel ground, dried, ground, and sieved.

According to one embodiment, a step of recovering fine powders after sieving the dried product of the hydrogel polymer; a step of reassembling the fine powders in the presence of a powder type of polymer binder to provide reassembled fine powders; and a step of mixing the reassembled fine powders with the hydrogel polymer before drying, are conducted.

The step of providing reassembled fine powders may include steps of dry mixing fine powders having an average particle diameter less than 150 µm and a powder type of polymer binder under a solvent-free condition, and then reassembling the fine powders through heat treatment.

Specifically, the binder used during the reassembly of fine powders should be free of organic solvents and harmful substances, should be harmless to a human body, should not contain volatile detection materials, should be able to reduce thermal losses of a moisture content of 5% or more, should have a maximized reaction area, should have Tm or Tg of equal to or less than a process temperature, and should have a low cost.

Thus, as a binder fulfilling all the requirements, a powder type of polymer binder that can exhibit excellent performance without a solvent is selected and used.

As such a powder type of polymer binder, polyethylene oxide powder having a weight average molecular weight of 100,000 to 600,000 g/mol is used.

Particularly, the polyethylene oxide powder has a lower melting point (Tm=65° C.) and glass transition temperature (Tg=−67° C.) than the reassembly process temperature, and has high Td. Further, since the polyethylene oxide powder has a large surface area compared to a water soluble polymer, it can exhibit a high binding effect and enables a water-free process.

Thus, by using the polyethylene oxide powder, processability can be improved.

Meanwhile, among the range of the weight average molecular weight of 100,000 to 600,000 g/mol, if a binder powder having a low molecular weight of closer to 100,000 is used, the reassembly efficiency can be further improved by increasing a binder content, a reassembly temperature, and a reassembly time.

In this case, the content of the powder type of polymer binder may preferably be about 50 to 100 parts by weight, among the range of 1 to 100 parts by weight, based on 100 parts by weight of the fine powders. In addition, the reassembly may be conducted at a temperature of 105° C. to 180° C. for 5 to 10 minutes.

Among the range of the weight average molecular weight of 100,000 to 600,000 g/mol, if a binder powder having a high molecular weight of closer to 600,000 is used, CRC can be further improved by decreasing the binder content, the reassembly temperature, and the reassembly time.

In this case, the content of the powder type of polymer binder may preferably be about 10 to 25 parts by weight, among the range of 1 to 100 parts by weight, based on 100 parts by weight of the fine powders. The reassembly may be conducted at a temperature of 105° C. to 180° C. for 5 to 10 minutes.

However, among the range of the weight average molecular weight of 100,000 to 600,000 g/mol, when a binder powder having a high molecular weight of closer to 600,000 is used, if a binder content is increased, binding and adhesion can be relatively improved.

Since the polyethylene oxide powder is mixed with fine powders in a dry state under a solvent-free condition and used, the amount of water (moisture content) used during the existing fine powder reassembly can be reduced, and particularly, thermal losses generated when evaporating water can be reduced.

Meanwhile, in the present invention, since polyethylene oxide is used in a powder state, heat energy in a specific temperature range is required to reassemble the fine powders. However, if the heat energy is excessively large or small, the reassembly efficiency may be lowered, and thus it is important to control the range.

Thus, it is preferable that the heat treatment is conducted at 105° C. to 180° C. for 10 to 20 minutes. If the heat treatment temperature is 105° C. or less, the reassembly efficiency may be lowered, and if is it 180° C. or more, thermal losses may be increased without an increase in reassembly efficiency. Further, if the heat treatment time is 10 minutes or less, the reassembly efficiency may be lowered, and if it is 20 minutes or more, thermal losses may be increased without an increase in reassembly efficiency.

The powder type of polymer binder may be used in an amount of 1 to 100 parts by weight, based on 100 parts by weight of the fine powders. More preferably, the polymer binder is used in an amount 10 to 100 parts by weight, based on 100 parts by weight of the fine powders. If the content of the powder type of polymer binder is less than 1 part by weight, the reassembly efficiency may be lowered, and if it is more than 100 parts by weight, a CRC value may be significantly decreased.

The reassembled fine powders may be additionally mixed with the hydrogel polymer before drying, and more specifically, between immediately before or immediately after the gel grinding step, and the drying step.

For example, the reassembled fine powders according to the present invention may be mixed in an amount of 10 to 30 parts by weight, or 15 to 28 parts by weight, based on 100 parts by weight of the hydrogel polymer before drying. Due to the additional introduction of the reassembled fine powders, the internal surface areas of base polymer powders and superabsorbent polymer may become broad, and the superabsorbent polymer may exhibit more improved absorption speed. Further, by the introduction of the reassembled fine powders of the above-explained content range, strengths of the base polymer powders and the superabsorbent polymer may be controlled to appropriate ranges, thus, effectively achieving the properties of one embodiment.

In the present invention, the reassembled fine powders may be ground using a hammer mill or a ball mill, and then sieved, and thus the reassembly efficiency according to each particle size may be measured. The reassembly efficiency is evaluated according to control of the degrees of grinding and sieving, and the method is not specifically limited. For example, if the sieving of the reassembled fine powders is minutely divided into 3 to 7 stages, the reassembly efficiency can be evaluated by the rate of the fine powders having an average particle size of less than 150 µm, after dividing the recovered fine powders with a mesh sieve and dividing them according to size.

According to the method of the present invention, the fine powder reassembly efficiency may be 14 to 76%, and the range may be variously controlled in the present invention.

A centrifuge retention capacity (CRC) of the reassembled fined powder of the present invention for a saline solution (0.9 wt % sodium chloride aqueous solution) for 30 minutes may be 9 g/g or more, and preferably 9.7 to 31.6 g/g. Although a higher CRC value is much better, since the present invention can efficiently obtain reassembled fine powders by further conducting a step of mixing the reassembled fine powders with the hydrogel polymer before drying, the productivity can be improved.

The centrifuge retention capacity (CRC) of the reassembled fined powder of the present invention for a saline solution may be calculated according to the following Equation 1, after a saline solution is absorbed into the reassembled fine powder for 30 minutes:

$$CRC(g/g)=\{[W_2(g)-W_1(g)-W_0(g)]/W_0(g)\}.$$  [Equation 1]

In Equation 1, $W_0$ (g) is the initial weight (g) of the reassembled fine powders, $W_1$ (g) is the weight of an envelope made of a non-woven fabric in which the reassembled fine powders are not included, measured after being impregnated with a saline solution for 30 minutes and then dehydrated using a centrifuge at 250 G for 3 minutes, and $W_2$ (g) is the weight of an envelope made of a non-woven fabric in which the reassembled fine powders are included, measured after being impregnated with a saline solution for 30 minutes and then dehydrated using a centrifuge at 250 G for 3 minutes.

Meanwhile, in the step of forming the hydrogel polymer, the hydrogel polymer including a first crosslinked polymer may be prepared through the crosslinking polymerization of a monomer composition including water soluble ethylenically unsaturated monomers, in the presence of an internal crosslinking agent.

The water soluble ethylenically unsaturated monomers may be any monomers commonly used in the preparation of superabsorbent polymer. As non-limiting examples, the water soluble ethylenically unsaturated monomer may be a compound represented by the following Chemical Formula 1:

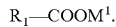

$$R_1\text{—}COOM^1.$$ [Chemical Formula 1]

In Chemical Formula 1, $R_1$ is a C2-5 alkyl group including an unsaturated bond, and $M^1$ is a hydrogen atom, a monovalent or divalent metal, an ammonium group, or an organic amine salt.

Appropriately, the monomers may be one or more selected from the group consisting of acrylic acid and methacrylic acid, and monovalent metal salts, divalent metal salts, ammonium salts, and organic amine salts of these acids. It is favorable for an acrylic acid or a salt thereof to be used as the water soluble ethylenically unsaturated monomer, because a superabsorbent polymer with improved absorption property can be obtained. In addition, as the monomers, one or more selected from the group consisting of anionic monomers and salts thereof selected from maleic anhydride, fumaric acid, crotonic acid, itaconic acid, 2-acryloylethane sulfonic acid, 2-methacryloylethane sulfonic acid, 2-(meth)acryloyl propane sulfonic acid, and 2-(meth)acrylamide-2-methylpropane sulfonic acid; non-ionic hydrophilic group-containing monomers selected from (meth)acrylamide, N-substituted (meth)acrylate, 2-hydroxyethyl (meth)acrylate, 2-hydroxypropyl (meth)acrylate, methoxy polyethylene glycol (meth)acrylate, and polyethylene glycol (meth)acrylate; and amino group-containing unsaturated monomers selected from (N,N)-dimethylaminoethyl (meth)acrylate and (N,N)-dimethylaminopropyl (meth)acrylamide, and quaternary products thereof, may be used.

Here, the water soluble ethylenically unsaturated monomers may have acid groups, and at least a part of the acid groups may be neutralized. Preferably, monomers that are partially neutralized with an alkali substance such as sodium hydroxide, potassium hydroxide, ammonium hydroxide, etc. may be used.

Here, the neutralization degree of the monomers may be 40 to 95 mol %, 40 to 80 mol %, or 45 to 75 mol %. Although the range of the neutralization degree may vary according to the final properties, if the neutralization degree is too high, neutralized monomers may be precipitated, thus rendering smooth progression of polymerization difficult, and to the contrary, if the neutralization degree is too low, the absorption of the polymer may be significantly lowered, and the polymer may exhibit a rubber-like property, such that it is difficult to handle.

The monomer composition may include a polymerization initiator commonly used in the preparation of a superabsorbent polymer. As non-limiting examples, as the polymerization initiator, a thermal polymerization initiator or a photo-polymerization initiator may be used according to polymerization methods. However, even in the case of photopolymerization, since a certain amount of heat is generated by UV irradiation, etc., and heat is generated to some degree according to the progression of an exothermic polymerization reaction, a thermal polymerization initiator may be additionally included.

As the photopolymerization initiator, one or more selected from the group consisting of benzoin ether, dialkyl acetophenone, hydroxyl alkyl ketone, phenyl glyoxylate, benzyl dimethyl ketal, acyl phosphine, and α-aminoketone may be used. Among them, as the acyl phosphine may include commercially available Lucirin TPO, i.e., 2,4,6-trimethyl-benzoyl-trimethyl phosphine oxide, it may be used. More various photopolymerization initiators are described in Reinhold Schwalm, "UV Coatings: Basics, Recent Developments and New Applications (Elsevier 2007)", page 115, and are not limited to the above-described examples.

As the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4$)$_2S_2O_8$), etc., and specific examples of the azo initiator may include 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, 4,4-azobis-(4-cyanovalericacid), etc. More various thermal initiators are described in "Principles of Polymerization (Wiley, 1981)", Odian, page 203, and are not limited to the above-described examples.

Such a polymerization initiator may be added at a concentration of about 0.001 to 1 wt %, based on the monomer composition. That is, if the concentration of the polymerization initiator is too low, the polymerization speed may become slow, and the remaining monomers may be extracted in a large quantity in the final product. To the contrary, if the concentration of the polymerization initiator is too high, the polymer chain making up a network may be shortened, and thus water soluble contents may increase and absorbency under pressure may be lowered, thus deteriorating the properties of the polymer.

Meanwhile, in the monomer composition, a crosslinking agent ("internal crosslinking agent") for the improvement of the properties of the polymer formed by the polymerization of the water soluble ethylenically unsaturated monomers is included. The crosslinking agent is for the internal crosslinking of the hydrogel polymer, and may be used separately from a "surface crosslinking agent" described below.

Particularly, in the preparation method, by using two or more kinds of internal crosslinking agents as explained above, for example, a polyol poly(meth)acrylate-based first internal crosslinking agent and an allyl (meth)acrylate-based second internal crosslinking agent together, a hydrogel polymer having higher gel strength, for example, 10,000 Pa or more, 11,000 Pa or more, or 120,000 Pa or more, and although not specifically limited, 50,000 Pa or less, 40,000 Pa or less, or 38,000 Pa or less, may be obtained.

More specifically, as the first internal crosslinking agent, one or more selected from the group consisting of trimethylolpropane tri(meth)acrylate, ethylene glycol di(meth)acrylate, polyethylene glycol di(meth)acrylate, propylene glycol di(meth)acrylate, polypropylene glycol di(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, and pentaerythritol tetraacrylate may be used, and as the second internal crosslinking agent, allyl methacrylate, allyl acrylate, etc. may be used.

The first internal crosslinking agent may be included in the content of 0.4 parts by weight to 1 part by weight, 0.5 to 0.9 parts by weight, or 0.6 to 0.8 parts by weight, based on 100 parts by weight of the monomer composition including the internal crosslinking agent, monomers, etc., and the second crosslinking agent may be included in the content of 0.008 to 0.5 parts by weight, 0.01 to 0.1 parts by weight, or 0.01 to 0.05 parts by weight, based on 100 parts by weight of the monomer composition. As such, by controlling the kinds and the content ranges of the internal crosslinking agents, and controlling the moisture content of the hydrogel polymer described below, a hydrogel polymer exhibiting gel strength of 10,000 Pa or more may be more effectively obtained, and a superabsorbent polymer fulfilling the properties of one embodiment may be more effectively obtained. However, if the content of the internal crosslinking agents is too high, basic absorption performance of the superabsorbent polymer may be deteriorated.

In addition, the monomer composition may further include additives such as a thickener, a plasticizer, a preservation stabilizer, an antioxidant, etc., as necessary.

Such a monomer composition may be prepared in the form of a solution in which the above-explained raw materials such as monomers, a polymerization initiator, internal crosslinking agents, etc. are dissolved in a solvent.

Here, the solvent that can be used is not limited in terms of its constitution as long as it can dissolve or disperse the above-explained raw materials, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methylethylketone, acetone, methyl amyl ketone, cyclohexanone, cyclopentanone, diethylene glycol monomethyl ether, diethylene glycol ethyl ether, toluene, xylene, butyrolactone, carbitol, methyl cellosolve acetate, N,N-dimethylacetamide, etc. may be used alone or in combination.

The formation of the hydrogel polymer through the polymerization of the monomer composition may be conducted by a common polymerization method, and the process is not specifically limited. As non-limiting examples, the polymerization method is largely classified into thermal polymerization and photopolymerization according to an energy source. Commonly, thermal polymerization may be progressed in a reactor equipped with a stirring axis such as a kneader, and photopolymerization may be progressed in a reactor equipped with a movable conveyer belt.

For example, the hydrogel polymer may be obtained by introducing the above-described monomer composition into a reactor equipped with a stirring axis such as a kneader, and supplying hot air or heating the reactor to progress thermal polymerization. Here, the hydrogel polymer discharged to the outlet of the reactor may be obtained in the size of a few centimeters to a few millimeters according to the shape of the stirring axis equipped in the reactor. Specifically, the size of the obtained hydrogel polymer may vary according to the concentration of the introduced monomer composition, the introduction speed, etc., and commonly, a hydrogel polymer with a (weight average) particle diameter of 2 to 50 mm may be obtained.

As another example, when photopolymerization of the monomer composition is progressed in a reactor equipped with a movable conveyer belt as described above, a hydrogel polymer in the form of a sheet may be obtained. Here, the thickness of the sheet may vary according to the concentration of the introduced monomer mixture and the introduction speed, but in order to uniformly polymerize the whole sheet, and simultaneously secure production speed, it is preferable for the thickness to be controlled to 0.5 to 10 cm.

The hydrogel polymer formed by the method may have a moisture content of 38 to 60 wt %, or 40 to 55 wt %. Here, the "moisture content" is the content of moisture occupied based on the total weight of the hydrogel polymer, and it means a value obtained by subtracting the weight of the polymer in a dry state from the weight of the hydrogel polymer.

Meanwhile, after forming the hydrogel polymer by the above-explained crosslinking polymerization, a step of gel grinding the hydrogel polymer is conducted.

In the step of gel grinding, the grinding of the hydrogel polymer may be conducted one or more times. Preferably, primary grinding and secondary grinding of the hydrogel polymer may be conducted.

In the gel grinding step, grinders that can be used in the gel grinding are not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, and a disc cutter may be used, but is not limited thereto.

For example, when the hydrogel polymer is ground twice, a disk type of cutter is used in the primary grinding process, and a chopper equipped with a screw is used in the secondary grinding. When using a chopper grinder, hot water may be introduced.

Meanwhile, the gel grinding of the hydrogel polymer may be conducted such that the particle diameter of the hydrogel polymer may become 0.1 mm to 10 mm. That is, in order to increase drying efficiency, it is preferable that the hydrogel polymer is ground to particles of a 10 mm diameter or less. However, since agglomeration between particles may be generated by excessive grinding, it is preferable that the hydrogel polymer is ground to particles of a 0.1 mm diameter or greater.

Further, since the gel grinding of the hydrogel polymer is conducted at a relatively low moisture content, adhering of the hydrogel polymer to the surface of a gel grinder may occur. In order to minimize such a phenomenon, steam, water, a surfactant, an anti-agglomeration agent (for example, clay, silica, etc.), a persulfate-based initiator, an azo-based initiator, hydrogen peroxide, a thermal polymerization initiator, an epoxy-based crosslinking agent, a diol crosslinking agent, a multi-functional crosslinking agent including an acrylate, a monofunctional crosslinking agent including a hydroxyl group, etc. may be added to the hydrogel polymer, as necessary.

After the gel grinding, the gel ground hydrogel polymer is dried, and the dried product of the hydrogel polymer is ground and sieved to form base polymer powders having an average particle diameter of 150 μm to 850 μm.

After the above process, the base polymer powders are transferred to a surface crosslinking process, and simultaneously, fine powders are recovered and a process of reassembling fine powders is conducted, and then the reassembled fine powders are re-introduced into the step of mixing with hydrogel polymer before drying, thus continuously conducting the steps of forming base polymer powders. The base polymer powders of the present invention may be prepared by a process further including the fine powder reassembly according to the above-explained method.

Specifically, the gel ground hydrogel polymer may be dried. The drying may be conducted at a temperature of 120 to 250° C., preferably 140 to 200° C., and more preferably 150 to 190° C. Here, the drying temperature may be defined as the temperature of a heating medium supplied for drying or the temperature inside of a drying reactor including a heat medium and polymer. If the drying temperature is low and the drying time lengthens, the process efficiency may be lowered, and thus, in order to prevent this, it is preferable that the drying temperature is 120° C. or more. Further, if the drying temperature is higher than necessary, the surface of the hydrogel polymer may be excessively dried and many fine powders may be generated in the subsequent grinding process, and the properties of the final polymer may be deteriorated, and in order to prevent this, it is preferable that the drying temperature is 250° C. or less.

Although a drying time in the drying step is not specifically limited, considering process efficiency, the properties of a polymer, etc., it may be controlled to 20 to 90 minutes under the above drying temperature.

The drying may be achieved using common media, and for example, it may be conducted by hot wind supply, infrared ray irradiation, ultrahigh frequency wave irradiation, UV irradiation, etc.

Preferably, the drying is conducted such that the dried polymer has a moisture content of about 0.1 to 10 wt %. That is, if the moisture content of dried polymer is less than 0.1 wt %, due to excessive drying, a preparation cost may increase and the degradation of crosslinked polymer may occur. Further, if the moisture content of the dried polymer is greater than 10 wt %, defects may be generated in the subsequent process.

After the drying, the dried polymer may be ground, and thereby the particle diameter and surface area of polymer may be controlled to appropriate ranges. The grinding may be conducted such that the particle diameter of the ground polymer becomes 150 to 850 μm.

As a grinder that can be used, common grinders such as a pin mill, a hammer mill, a screw mill, a roll mill, a disc mill, a jog mill, etc. may be used.

In order to manage the properties of the finally produced superabsorbent polymer, a step of selectively sieving particles having a particle diameter of 150 to 850 μm in the polymer particles obtained through the grinding step may be further conducted.

Meanwhile, after passing through the above-explained sieving process to prepare base polymer powders, in the presence of a surface crosslinking agent, the base polymer powders may be heat treated and surface crosslinked to form superabsorbent polymer particles.

The surface crosslinking induces a crosslinking reaction on the surface of the base polymer powders in the presence of a second crosslinking agent (surface crosslinking agent), and through the surface crosslinking, a surface modification layer (surface crosslink layer) may be formed on the surface of the base polymer powders.

The surface crosslinking may be conducted, for example, by mixing a solution including a second crosslinking agent (surface crosslinking agent) with the base polymer powders to progress a crosslinking reaction.

Here, the surface crosslinking agent is a compound capable of reacting with the functional group of the polymer, and an alkylene carbonated-based compound or a polyhydric alcohol compound may be used, and C2-5 alkylene carbonated is preferable. More preferably, as the surface crosslinking agent, ethylene carbonate may be used. In addition to the surface crosslinking agent, silica or clay may be used. In order to control the penetration speed and depth of the surface crosslinking agent, if necessary, an acidic compound or polymer may be additionally added.

Here, the content of the surface crosslinking agent may be appropriately controlled according to the kind of the crosslinking agent, reaction conditions, etc., and preferably, it may be controlled to 0.001 to 5 parts by weight, based on 100 parts by weight of the base polymer powders. If the content of the surface crosslinking agent is too low, surface modification may not be properly achieved, and thus the properties of the final polymer may be deteriorated. To the contrary, if an excessive amount of the surface crosslinking agent is used, due to an excessive surface crosslinking reaction, basic absorption performance of the polymer may be deteriorated.

Meanwhile, the surface crosslinking step may be conducted by putting a surface crosslinking solution and base polymer powders in a reactor and mixing them, spraying a surface crosslinking solution onto the base polymer powders, continuously feeding the base polymer powders and surface crosslinking solution to a continuously operated mixer, or the like.

Further, when adding the surface crosslinking agent, water may be additionally added. As such, by adding water together with the surface crosslinking agent, uniform dispersion of the surface crosslinking agent may be induced, agglomeration of base polymer powders may be prevented, and the penetration depth of the surface crosslinking agent for the base polymer powders may be more optimized. Considering such aims and effects, the content of water added together with the surface crosslinking agent may be controlled to 0.5 to 10 parts by weight, based on 100 parts by weight of the base polymer powders.

The surface crosslinking step may be progressed at a temperature of 100 to 250° C. Further, the surface crosslinking may be progressed for 1 to 120 minutes, preferably 1 to 100 minutes, and more preferably 10 to 80 minutes. That is, in order to minimally induce a surface crosslinking reaction and simultaneously prevent the deterioration of the properties due to damage to the polymer during excessive reaction, the surface crosslinking step may be conducted under above-explained conditions.

Meanwhile, according to another embodiment of the present invention, a superabsorbent polymer is provided, which includes: base polymer powders including a first crosslinked polymer of water soluble ethylenically unsaturated monomers having acid groups of which at least a part are neutralized; and a surface crosslink layer formed on the base polymer powders and including a second crosslinked polymer in which the first crosslinked polymer is additionally crosslinked by a surface crosslinking agent, wherein a centrifuge retention capacity (CRC) for a saline solution (0.9 wt % sodium chloride aqueous solution) for 30 minutes is 30 g/g to 45 g/g.

The superabsorbent polymer of one embodiment may fulfill the basic properties required, and simultaneously exhibit an excellent absorption ratio. In addition, the superabsorbent polymer may exhibit excellent permeability because the surface crosslinking of base polymer powders is progressed and the superabsorbent polymer includes a surface crosslink layer.

Further, the superabsorbent polymer of one embodiment may have an average particle diameter of about 150 to 850 μm or about 300 to 500 μm. More specifically, 95 wt % or more of the base polymer powders and superabsorbent polymer including the same may have a particle diameter of 150 to 850 μm, and less than 3 wt % thereof may be fine powders having a particle diameter of less than 150 μm.

Advantageous Effects

The present invention can provide a method for preparing a superabsorbent polymer that does not use water during the process of reassembling fine powders of the superabsorbent polymer, thus reducing thermal losses, and reassembles fine powders using a specific polymer binder powder, thus maintaining excellent basic absorption performances, and simultaneously improving productivity.

BRIEF DESCRIPTION OF THE DRAWINGS

FIG. 1 shows scanning electron microscope photographs of reassembled fine powders used in Examples 8 and 9 of the present invention.

DETAILED DESCRIPTION OF THE EMBODIMENTS

Hereinafter, preferable examples are presented for better understanding of the present invention. However, these examples are presented only as the illustrations of the present invention, and the present invention is not limited thereby.

Examples 1 to 8

As an apparatus for preparing a superabsorbent polymer, a continuous preparation apparatus performing a polymerization process, a hydrogel grinding process, a drying process, a grinding process, a sieving process, a surface crosslinking process, a cooling process, a sieving process, and a transportation process connecting each process, was used.

(Step 1)
Step of Forming Hydrogel Polymer 100 parts by weight of acrylic acid were mixed with 0.7 parts by weight (7000 ppm) of polyethylene glycol diacrylate (weight average molecular weight: ~500 g/mol) and 0.015 parts by weight of allyl methacrylate as internal crosslinking agents, and with 0.01 parts by weight of IRGACURE 819 as a photoinitiator to prepare a monomer solution. Subsequently, while the monomer solution was continuously fed with a metering pump, 160 parts by weight of an aqueous solution of 24 wt % sodium hydroxide was line-mixed to prepare an aqueous solution of monomers. At this time, the temperature increase by the heat of neutralization was controlled to 40° C. After continuous line mixing of 6 parts by weight of an aqueous solution of 4 wt % sodium persulfate, the mixture was continuously fed to a continuous polymerization reactor having a planar polymerization belt equipped with embankments at both ends. Thereafter, UV was irradiated for 1 minute, and thermal polymerization was additionally progressed for 2 minutes to prepare a hydrogel polymer. The moisture content of such hydrogen polymer was confirmed to be 45 wt %.

(Step 2)
Step of Grinding Hydrogel Polymer

The hydrogel polymer was primarily cut using a cutter such that the average size became about 300 mm or less, and then it was introduced into a chopper together with reassembled fine powders, and secondarily ground. Here, as the reassembled fine powders, the reassembled fine powders prepared in step 5 below were used, and the introduction rate was 20 parts by weight, based on 100 parts by weight of the hydrogel polymer.

(Step 3)
Step of Drying Gel Ground Hydrogel Polymer

Subsequently, the hydrogel ground in step 2 was dried in a dryer capable of transferring wind up and down. Hot air was flowed from the lower side to the upper side for 15 minutes, and was flowed again from the upper side to the lower side for 15 minutes, so that the moisture content of dried powder became about 2% or less, thus uniformly drying the hydrogel.

(Step 4)
Step of Forming Base Polymer Powders

The hydrogel polymer dried in step 3 was ground with a grinder and then sieved to obtain a base polymer with a size of 150 to 850 μm.

Meanwhile, fine powders, i.e., polymer particles having a particle diameter of less than 150 μm, were recovered through the sieving, and then reassembled fine powders were prepared according to step 5 below, and used as the reassembled fine powders of step 2.

(Step 5)
Step of Providing Reassembled Fine Powders (Reassembly of Fine Powders with Moisture Content of 0%)

Fine powders, i.e., polymer particles having a particle diameter of less than 150 μm, were recovered through the sieving, and then introduced into a mixer and dry-mixed under a solvent-free condition together with PEO powders (Mw=100,000 g/mol). The PEO powders were used while changing the content based on 100 parts by weight of the total fine powders. That is, the PEO powders were used in an amount of 1, 5, 10, 15, 25, 50, 75, and 100 parts by weight, respectively, which were divided as Examples 1 to 8. As the mixer, one equipped with a stirring means and a temperature control means was used.

After the dry mixing was completed, heat treatment was progressed at 105 t for 10 minutes to prepare reassembled fine powders.

(Step 6)
Step of Forming Superabsorbent Polymer Particles

Thereafter, 100 parts by weight of the base polymer prepared in step 4 were mixed with a crosslinking solution including 4 parts by weight of water and 1 part by weight of ethylene carbonate, and then subjected to a surface crosslinking reaction at 180° C. for 40 minutes. The obtained product then was cooled and sieved to obtain a superabsorbent polymer of which the surface was crosslinked, and having a particle diameter of 150 to 850 μm.

Example 9

A superabsorbent polymer was prepared by the same method as Example 8, except that the heat treatment temperature was changed to 180° C., in the process of reassembling the fine powders of step 5.

Comparative Example 1

A superabsorbent polymer was prepared by the same method as Example 8, except that after mixing the fine powders with water, reassembly was progressed, and a process of drying the moisture of the reassembled fine powders was progressed in a separate drier, in the process of reassembling fine powders of step 5.

That is, based on 100 parts by weight of fine powders, 125 parts by weight of water were mixed with the fine powders in a mixer to progress reassembly of fine powders (using a kneader: 650 rpm, 1 minute). After mixing the fine powders with water, moisture drying was progressed (180° C., 1 hour).

Comparative Example 2

A superabsorbent polymer was prepared by the same method as Example 8, except that based on 100 parts by weight of the fine powders, 10 g of the aqueous solution of polypropylene glycol (moisture content 10%) was used, in the process of reassembling the fine powders of step 5.

However, due to the use of the polypropylene glycol aqueous solution, after reassembling the fine powders, a moisture drying process was progressed in a separate drier like Comparative Example 1 (moisture drying conditions: 180° C., 1 hour).

Comparative Example 3

A superabsorbent polymer was prepared by the same method as Example 8, except that the heat treatment was progressed at 180° C. for 9 minutes, in the process of reassembling the fine powders of step 5.

As the result of progressing heat treatment for less than 10 minutes, the reassembly efficiency of the fine powders was lowered to decrease productivity.

Experimental Example 1

For the reassembled fine powders of Examples 8 and 9, average particle diameters were measured using a scanning electron microscope photograph, and are shown in FIG. 1.

As shown in FIG. 1, it can be seen that the reassembled fine powders of Examples 8 and 9 have excellent binding and cohesion.

Experimental Example 2

The reassembled fine powders of Examples 8 and 9 were ground and sieved by the method of the following Table 1, and then the reassembly efficiency and CRC were measured and the results are shown in Table 2.

That is, the reassembled fine powders of the examples were ground using a hammer mill or a ball mill, and then, using a mesh sieve, they were divided into 3 or 7 stages, and the reassembly efficiencies and CRCs were measured (3 stages: sieved into stages of #30 top, #30~50, #50 bottom according to the sieve particle size, 7 stages: sieved into #20 top, #20~30, #30~40, #40~50, #50~70, #70~100, #100 bottom according to the sieve particle size).

Hammer mill (grinding conditions: 650 rpm, grinding until a torque value of 4 is reached)

Ball mill (grinding conditions: 300 rpm, 20 minutes, using 10 ceramic balls)

In case the reassembled fine powders are sieved into 3 stages or 7 stages, the reassembly efficiency can be measured according to the following calculation formulae.

3 stage classification: reassembly efficiency=(the amount of #30 top+the amount of #30~50)/total amount of fine powders*100      [Calculation Formula 2]

7 stage classification: reassembly efficiency=(the amount of #20~30+the amount of #30~40+the amount of #40~50+the amount of #50~70+the amount of #70~100)/total amount of fine powders*100      [Calculation Formula 3]

TABLE 1

| Example | Content of binder (parts by weight) | Rates according to particle size (wt %) | | | | | | |
|---|---|---|---|---|---|---|---|---|
| | | #20 top | #20~30 | #30~40 | #40~50 | #50~70 | #70~100 | #100 bottom |
| 1 | 1 | 0.56 | 0.41 | 0.71 | 1.62 | 2.28 | 9.02 | 85.40 |
| 2 | 5 | 0.80 | 0.35 | 0.80 | 1.50 | 2.89 | 12.36 | 81.31 |
| 3 | 10 | 1.46 | 1.36 | 3.98 | 9.77 | 12.4 | 15.16 | 55.82 |
| 4 | 15 | | | | | | | |
| 5 | 25 | 0.66 | 0.61 | 2.29 | 7.88 | 13.68 | 19.63 | 55.24 |
| 6 | 50 | | | | | | | |
| 7 | 75 | | | | | | | |
| 8 | 100 | | | | | | | |

TABLE 2

| Example | Content of binder (parts by weight) | Reassembly efficiency 1 (%) | Reassembly efficiency 2 (%) | Reassembly efficiency 3 (%) | CRC [g/g] |
|---|---|---|---|---|---|
| 1 | 1 | 14.0 | 3.3 | | 31.6 |
| 2 | 5 | 17.9 | 6.3 | | 25.2 |
| 3 | 10 | 42.7 | 29.0 | 13.2 | 22.0 |
| 4 | 15 | | | 20.7 | 21.2 |
| 5 | 25 | 44.1 | 25.1 | 40.7 | 21.6 |
| 6 | 50 | | | 55.6 | 15.9 |

TABLE 2-continued

| Example | Content of binder (parts by weight) | Reassembly efficiency 1 (%) | Reassembly efficiency 2 (%) | Reassembly efficiency 3 (%) | CRC [g/g] |
|---|---|---|---|---|---|
| 7 | 75 | | | 62.4 | 12.6 |
| 8 | 100 | | | 74.1 | 9.7 |

Reassembly efficiency 1: using ball mill grinding and 7 stage classification method
Reassembly efficiency 2: using ball mill grinding and 3 stage classification method
Reassembly efficiency 3: using hammer mill grinding and 3 stage classification method Experimental Example 3

For the reassembled fine powders of Comparative Examples 1 and 2, the reassembly efficiencies, CRCs, and water absorption speeds were measured by common methods. The results are shown in the following Table 3.

TABLE 3

| Comparative Example | Moisture content (%) | Content of PPG aqueous solution binder (parts by weight) | Reassembly efficiency (%) | CRC [g/g] | Water absorption speed |
|---|---|---|---|---|---|
| 1 | 56 | | 68 | 35.1 | 1 |
| 2 | 10 | 10 | No reassembly effect | | |

As shown in the Table 3, although Comparative Example 1 fulfilled the reassembly efficiency and CRC of certain levels, a separate drying process should be progressed due to a high moisture content. Further, Comparative Example 2 required a drying process despite a low moisture content, and particularly, it could not exhibit the reassembly effect, and thus was inefficient.

Thus, it can be seen that in the case of Comparative Examples 1 and 2, a process is lengthened due to the separate drying process, and energy loss is generated.

Experimental Example 4

The CRC of each superabsorbent polymer prepared in Example 1 and Comparative Example 2 was measured and evaluated as follows.

Centrifuge Retention Capacity (CRC)

Centrifuge retention capacity (CRC) according to absorption rate under no load was measured according to EDANA (European Disposables and Nonwovens Association) standard EDANA WSP 241.3. $W_0$ (g, about 0.2 g) of the superabsorbent polymer were uniformly put in an envelope made of a non-woven fabric, and the envelope was sealed. The envelope was then soaked in a 0.9 wt % sodium chloride aqueous solution (saline solution) at room temperature. After 30 minutes, the envelope was drained at 250 G for 3 minutes using a centrifuge, and the mass $W_2$ (g) of the envelope was measured. After the same operation without using superabsorbent polymer, the mass $W_1$ (g) at that time was measured. Using the obtained weights, CRC (g/g) of superabsorbent polymer was calculated according to the following Calculation Formula 4, thus confirming centrifuge retention capacity.

$$CRC(g/g) = \{[W_2'(g) - W_1'(g) - W_0'(g)] / W_0'(g)\} \quad \text{[Calculation Formula 4]}$$

The property values of Example 1 and Comparative Example 2 measured by the above method are summarized in the following Table 4.

TABLE 4

| Unit | CRC g/g |
|---|---|
| Example 1 | 31.6 |
| Comparative Example 2 | 23.0 |

Referring to Table 4, it can be seen that Example 1 of the present invention exhibits properties that are equivalent to or much better than those of Comparative Example 2, and particularly, exhibits much better basic absorption performance defined as CRC.

The invention claimed is:

1. A method for preparing a superabsorbent polymer, comprising:
    conducting crosslinking polymerization of water soluble ethylenically unsaturated monomers comprising monomers having acid groups of which at least a part are neutralized, in the presence of an internal crosslinking agent, to form a hydrogel polymer comprising a first crosslinked polymer;
    gel grinding the hydrogel polymer to form a gel ground hydrogel polymer;
    drying the gel ground hydrogel polymer, and grinding and sieving the dried hydrogel polymer to form base polymer powders; and
    heat treating the base polymer powders to progress surface crosslinking, in the presence of a surface crosslinking agent to produce the superabsorbent polymer,
    wherein the method further comprises:
    recovering fine powders, after sieving the dried hydrogel polymer;
    reassembling the fine powders in the presence of a powder type of polymer binder to provide reassembled fine powders; and
    introducing the reassembled fine powders in the step of gel grinding the hydrogel polymer to mix the reassembled fine powders with the hydrogel polymer before drying,
    wherein the powder type of polymer binder consists of polyethylene oxide powders having a weight average molecular weight of 100,000 to 600,000 g/mol.

2. The method for preparing a superabsorbent polymer according to claim 1, wherein the fine powders have an average particle diameter less than 150 μm and wherein the reassembling the fine powders comprises dry mixing the fine powders and the powder type of polymer binder under a solvent-free condition, and then reassembling the fine powders through heat treatment.

3. The method for preparing a superabsorbent polymer according to claim 2, wherein the heat treatment is conducted at 105 to 180° C. for 10 to 20 minutes.

4. The method for preparing a superabsorbent polymer according to claim 1, wherein the powder type of polymer binder is used in an amount of 1 to 100 parts by weight, based on 100 parts by weight of the fine powders.

5. The method for preparing a superabsorbent polymer according to claim 1, wherein the reassembled fine powders are mixed in an amount of 10 to 30 parts by weight, based on 100 parts by weight of the hydrogel polymer before drying.

6. The method for preparing a superabsorbent polymer according to claim 1, wherein the gel grinding of the hydrogel polymer is conducted two or more times.

7. The method for preparing a superabsorbent polymer according to claim 1, wherein the water soluble ethylenically unsaturated monomers include one or more of anionic monomers and salts thereof selected from acrylic acid, methacrylic acid, maleic anhydride, fumaric acid, crotonic acid, itaconic acid, 2-acryloylethane sulfonic acid, 2-methacryloylethane sulfonic acid, 2-(meth)acryloyl propane sulfonic acid, and 2-(meth)acrylamide-2-methylpropane sulfonic acid; non-ionic hydrophilic group-containing monomers selected from (meth)acrylamide, N-substituted (meth)acrylate, 2-hydroxyethyl (meth)acrylate, 2-hydroxypropyl (meth)acrylate, methoxy polyethylene glycol (meth) acrylate, and polyethylene glycol (meth)acrylate; or amino group-containing unsaturated monomers selected from (N,N)-dimethylaminoethyl (meth)acrylate, (N,N)-dimethylaminopropyl (meth)acrylamide, and quaternized products thereof.

8. The method for preparing a superabsorbent polymer according to claim 1, wherein the first crosslinked polymer includes a polymer formed by the crosslinking polymerization of the water soluble ethylenically unsaturated monomers, in the presence of a polyol poly(meth)acrylate-based first internal crosslinking agent selected from the group consisting of trimethylolpropane tri(meth)acrylate, ethylene glycol di(meth)acrylate, polyethylene glycol di(meth)acrylate, propylene glycol di(meth)acrylate, polypropylene glycol di(meth)acrylate, butanediol di(meth)acrylate, butylene glycol di(meth)acrylate, diethylene glycol di(meth)acrylate, hexanediol di(meth)acrylate, triethylene glycol di(meth) acrylate, tripropylene glycol di(meth)acrylate, tetraethylene glycol di(meth)acrylate, dipentaerythritol pentaacrylate, glycerin tri(meth)acrylate, and pentaerythritol tetraacrylate; and an allyl(meth)acrylate-based second internal crosslinking agent.

9. The method for preparing a superabsorbent polymer according to claim 1, wherein the internal crosslinking agent includes a polyol poly(meth)acrylate-based first internal crosslinking agent and an allyl (meth)acrylate-based second internal crosslinking agent, and
the first internal crosslinking agent is included in a content of 0.4 parts by weight to 1 part by weight, based on 100 parts by weight of a monomer composition comprising the internal crosslinking agent and water soluble ethylenically unsaturated monomers, and the second internal crosslinking agent is included in a content of 0.008 parts by weight to 0.5 parts by weight, based on 100 parts by weight of the monomer composition.

10. The method for preparing a superabsorbent polymer according to claim 1, wherein the surface crosslinking agent includes an alkylene carbonate-based compound or a polyhydric alcohol compound.

11. The method for preparing a superabsorbent polymer according to claim 1, wherein the powder type of polymer binder is used in an amount of 10 to 25 parts by weight, based on 100 parts by weight of the fine powders.

12. A superabsorbent polymer comprising:
base polymer powders comprising a first crosslinked polymer of water soluble ethylenically unsaturated monomers having acid groups of which at least a part are neutralized;
a surface crosslink layer formed on the base polymer powders, and comprising a second crosslinked polymer in which the first crosslinked polymer is additionally crosslinked by a surface crosslinking agent;
reassembled fine powders; and
a powder type of polymer binder consisting of polyethylene oxide powders having a weight average molecular weight of 100,000 to 600,000 g/mol;
wherein a centrifuge retention capacity (CRC) of the superabsorbent polymer for a saline solution having 0.9 wt % sodium chloride in aqueous solution for 30 minutes is 30 g/g to 45 g/g.

13. The superabsorbent polymer according to claim 12, wherein the superabsorbent polymer has a particle diameter of 150 to 850 μm.

* * * * *